United States Patent
Arizti et al.

(10) Patent No.: US 8,663,183 B2
(45) Date of Patent: *Mar. 4, 2014

(54) ABSORBENT ARTICLES WITH COMFORTABLE ELASTICATED LAMINATES

(75) Inventors: Blanca Arizti, Frankfurt am Main (DE); Ekaterina Anatolyevna Ponomarenko, Bad Soden (DE); Gemma Baquer Molas, Schwalbach (DE); Simone Seeboth, Schwalbach (DE); David James Dahlinger, Mason, OH (US); David Richard Tucker, Mason, OH (US); Don Randell Greer, Lockland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 667 days.

This patent is subject to a terminal disclaimer.

(21) Appl. No.: 11/645,389

(22) Filed: Dec. 26, 2006

(65) Prior Publication Data

US 2007/0197993 A1   Aug. 23, 2007

(30) Foreign Application Priority Data

Dec. 28, 2005   (EP) ..................................... 05113018

(51) Int. Cl.
  *A61F 13/15*   (2006.01)
(52) U.S. Cl.
  USPC ................................ 604/385.26; 604/385.28
(58) Field of Classification Search
  USPC ........................................ 604/385.26–385.28
  See application file for complete search history.

(56) References Cited

U.S. PATENT DOCUMENTS

| 4,657,539 | A | * | 4/1987 | Hasse ....................... 604/385.25 |
| 4,795,452 | A | * | 1/1989 | Blaney et al. ............. 604/385.27 |
| 5,322,729 | A |   | 6/1994 | Heeter et al. |
| 5,607,760 | A |   | 3/1997 | Roe |
| 5,876,753 | A |   | 3/1999 | Timmons et al. |
| 5,888,591 | A |   | 3/1999 | Gleason et al. |

(Continued)

FOREIGN PATENT DOCUMENTS

| EP | 1201212 | 6/2002 |
| WO | WO-95/24173 A3 | 10/1995 |
| WO | WO-96/03501 A1 | 2/1996 |
| WO | WO-03059603 A1 | 7/2003 |

OTHER PUBLICATIONS

International Search Report, Jun. 5, 2007.

*Primary Examiner* — Lynne Anderson
(74) *Attorney, Agent, or Firm* — Andrew J. Mueller; William E. Gallagher

(57) ABSTRACT

A disposable absorbent article is claimed that comprised a backsheet and an absorbent core and a core coversheet or topsheet, that in use faces the wearer, and one or more cuffs (25, 26), comprising one or more longitudinally extending elastic laminate portion(s) (10), formed by at least an elastic material (12) attached to a supporting sheet (20) of said cuff (25, 26), said laminate portion(s) (10) comprising in at least relaxed and partially contracted state a body-facing surface with a multitude of wrinkles, and whereby said elastic laminate portion (10) has an absolute contracted length $L_c$ and a fully stretched absolute length $L_s$,
  whereby at a partial elongation of the elastic laminate potion (10) of $\epsilon=0.5$:
  a) said wrinkles have an average wrinkle height $H_w$ of less than 600 micrometers; and
  b) said laminate portion (10) has an average wrinkle density $D_w$ between 5 and 10 wrinkles per cm.

13 Claims, 5 Drawing Sheets

(56) References Cited

U.S. PATENT DOCUMENTS

| | | | |
|---|---|---|---|
| 6,045,877 A | 4/2000 | Gleason et al. | |
| 6,451,001 B2 * | 9/2002 | Kumasaka | 604/385.27 |
| 6,569,140 B1 | 5/2003 | Mizutani et al. | |
| 6,624,340 B2 | 9/2003 | Mizutani et al. | |
| 6,648,869 B1 * | 11/2003 | Gillies et al. | 604/385.28 |
| 7,048,726 B2 * | 5/2006 | Kusagawa et al. | 604/385.28 |
| 2001/0056268 A1 | 12/2001 | Mizutani et al. | |
| 2002/0157771 A1 | 10/2002 | Kusagawa et al. | |
| 2004/0162538 A1 * | 8/2004 | Mueller et al. | 604/385.01 |
| 2005/0084656 A1 | 4/2005 | Ukegawa et al. | |
| 2005/0095942 A1 | 5/2005 | Mueller et al. | |
| 2006/0111686 A1 * | 5/2006 | Schneider | 604/385.26 |
| 2007/0088307 A1 | 4/2007 | Arizti et al. | |
| 2007/0088309 A1 * | 4/2007 | Ehrnsperger et al. | 604/385.28 |
| 2007/0093771 A1 | 4/2007 | Arizti et al. | |
| 2007/0197994 A1 * | 8/2007 | Arizti et al. | 604/385.26 |

* cited by examiner

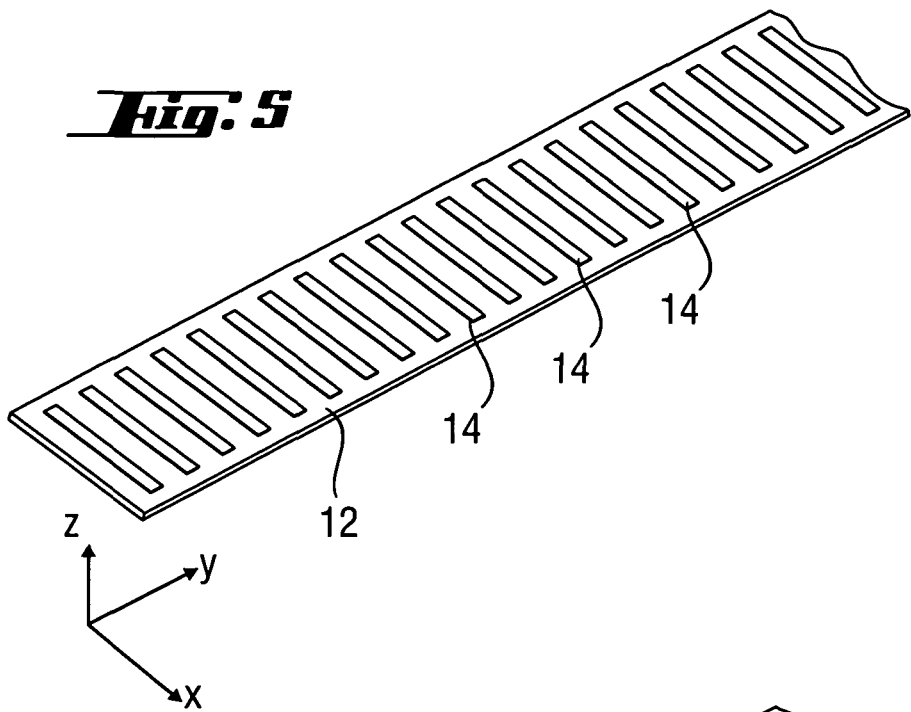
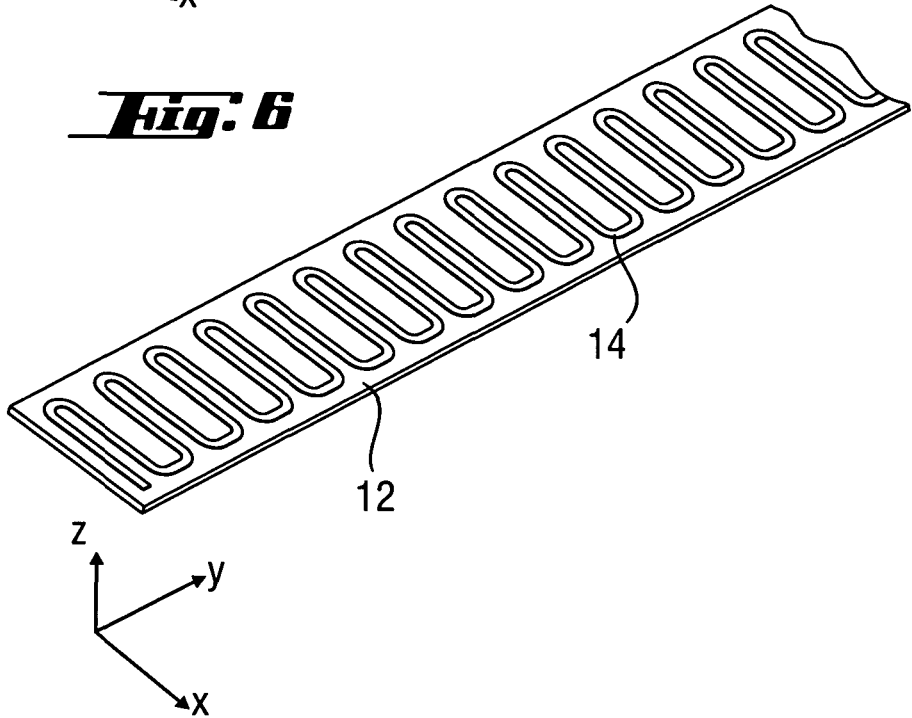

ABSORBENT ARTICLES WITH COMFORTABLE ELASTICATED LAMINATES

FIELD OF THE INVENTION

This invention relates to disposable absorbent articles comprising leg cuffs or barrier cuffs (25, 26) that comprises one or more elastic laminate portion(s) (10) with substantially y-directional or longitudinal (stretch), formed from a supporting material (20), and an elastic material (12) (and optionally an attachment means and/or attachment sheet and/or cover strip (13)), whereby said elastic laminate portions (10) have wrinkles of a very low wrinkle height and a selected average wrinkle density, in order to reduce the risk of severe pressure marks. The elastic laminate portion(s) (10) are preferably very thin. The provision of such elastic laminate portions (10) still provides an excellent force profile for the cuff. Overall, comfortable-to-wear absorbent articles are obtained that have excellent leg seals that cause very little or no pressure marks in use.

BACKGROUND OF THE INVENTION

Absorbent articles such as infant diapers, training pants and adult incontinence garments typically comprise elastic leg cuffs and or barrier cuffs to reduce leakage of exudates from the article. Often, they also comprise an elasticated waist band, to improve the fit and comfort when the wearer is moving.

These elasticated portions of such articles typically comprise an elastic material laminated to a non-elastic sheet, such as a plastic film, or nonwoven material, obtained by attaching the elastic material in stretched state to the sheet. The resulting laminate thus comprises in unstretched, contracted state and in partially stretched state a surplus of sheet material that forms wrinkles.

Such elasticated portions of the diaper can be uncomfortable in use, due to the pressure of the elastic portions on the skin and/or due to rubbing of the wrinkled elasticated portions over the skin.

The inventors have also found that even if the user does not experience the elasticated portions as uncomfortable, the red skin marks caused by the elasticated portions may still be perceived by the care taker as uncomfortable for the user.

The inventors have found that this problem can be ameliorated by use of elastic laminate portion(s) that, at least on the surface that faces the body in use, have wrinkles of (on average) a very small z-dimensions (height), and that have a very selected wrinkle density (wrinkles per cm). They found that such elastic laminate portions leave at the most very minor, shallow pressure marks (wrinkle indentations) on the skin, that disappear very quickly and that are (perceived as) less troublesome. Furthermore, if such minor pressure marks are still formed, they are believed to create less of a risk of skin irritation. They also found that it is beneficial that the elastic laminate portions(s) are very thin, at least in the free edge area.

Thus, absorbent articles are provided that still maintain an excellent elastic profile and performance and that at the same type have a highly reduced, or no pressure mark problem and that are more comfortable in use.

SUMMARY OF THE INVENTION

The invention relates to a disposable absorbent article comprising a backsheet and an absorbent core and a core coversheet or topsheet, that in use faces the wearer, and one or more cuffs (25, 26), comprising one or more longitudinally extending elastic laminate portion(s) (10), formed by at least an elastic material (12) attached to a supporting sheet (20) of said cuff (25, 26), said laminate portion(s) (10) comprising in at least relaxed and partially contracted state a body-facing surface with a multitude of wrinkles, and whereby said elastic laminate portion (10) has an absolute contracted length $L_c$ and a fully stretched absolute length $L_s$, whereby at a partial elongation of the elastic laminate potion (10) of $\epsilon=0.5$:
a) said wrinkles have an average wrinkle height $H_w$ of less than 600 micrometers; and
b) said laminate portion (10) has an average wrinkle density $D_w$ between 5 and 10 wrinkles per cm.

Said elastic laminate portion (10) has in one embodiment an average caliper (at 0.33 psi and at an elongation $\epsilon=0.5$) from 0.4 mm (400 microns) to 1.3 mm, typically to 1.0 mm.

The article is preferably a diaper, e.g. an adult incontinence garment, baby or infant diaper or training pants.

Furthermore, the inventors have found that pressure marks may result in skin irritation if the pressure marks are caused by hydrophilic elastic material that may be wet in use, because the wetness can increase the skin irritation. Thus, the inventors have found that it is beneficial to ensure that such the supporting sheet material (20), e.g. the nonwoven material, forming part of the laminate portions, are hydrophobic.

It may be preferred that the supporting sheet (20) itself is not elastically stretchable in y-direction.

The elastic laminate portions as described herein can also be used as (part of) the elastic waistband and/or the elastic side panels.

BRIEF DESCRIPTION OF THE DRAWINGS

FIG. 5 shows an exemplary attachment (adhesive) pattern with attachment adhesive areas (14) that may be used to attach the elastic material to the supporting sheet material (20) or other material comprised in the elastic laminate portion, as described herein.

FIG. 6 shows an alternative attachment (adhesive) pattern with attachment areas (14) that may be used to attach the elastic material to the supporting sheet material (20) or other material comprised in the elastic laminate portion, as described herein.

DETAILED DESCRIPTION OF THE INVENTION

Figure 1:
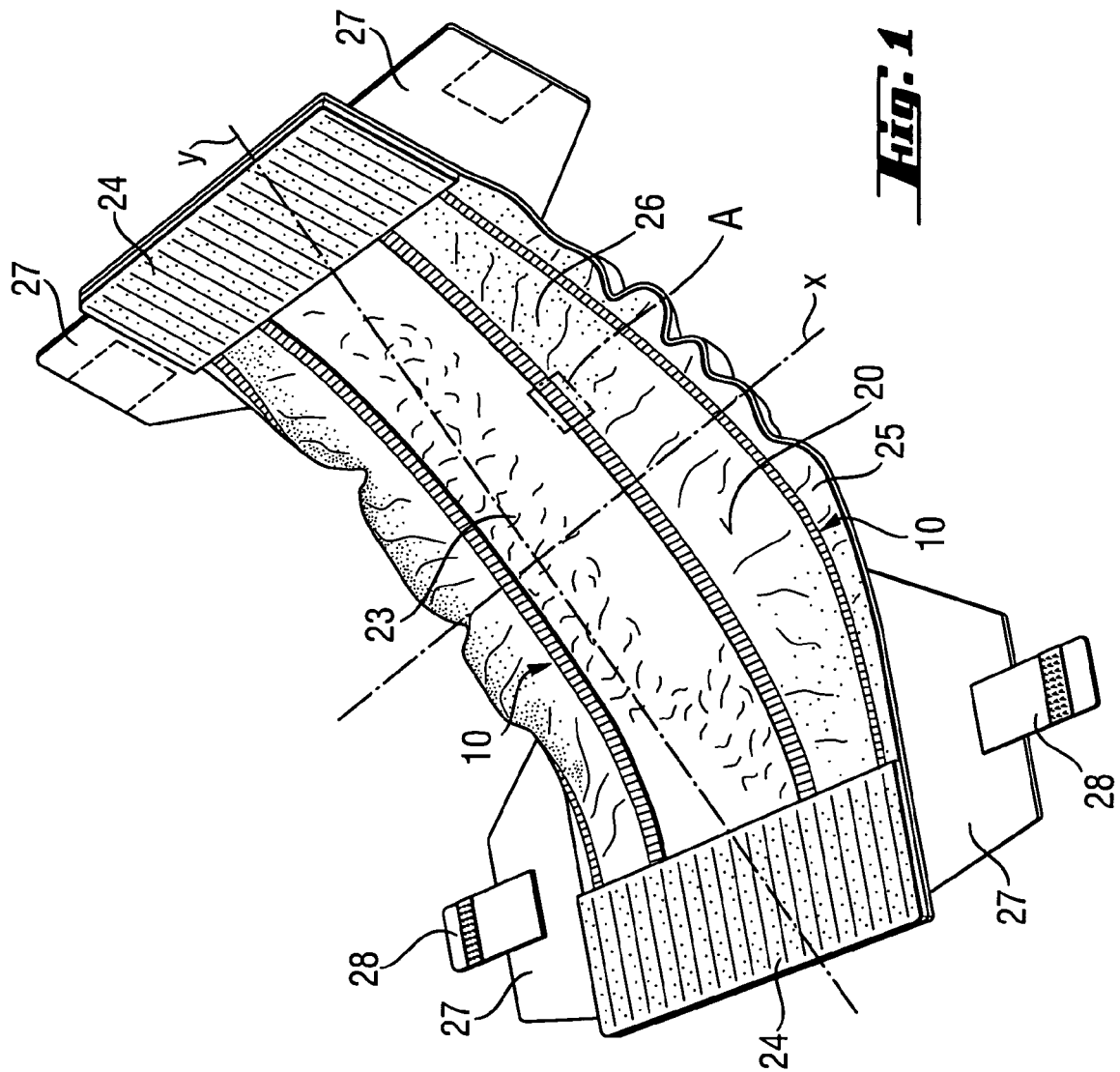
FIG. 1 shows a perspective view of an exemplary diaper of the present invention

"Absorbent article" refers to wearable devices, which absorb and/or contain liquid, and more specifically, refers to devices, which are placed against or in proximity to the body of the wearer to absorb and contain the various exudates discharged from the body. As used herein, the term "diaper" refers to an absorbent article generally worn by infants and incontinent people about the lower torso.

"y-direction" elongation or stretch as used herein means that the cuff (25, 26) or laminate portion (10) has as a whole an elongation or stretch in an average direction, that is herein referred to as "y-direction". This may be a direction within 45 degrees of the longitudinal axis or line parallel thereto of the cuff (25, 26) or elastic laminate portion (10).

"Absolute filly stretched length" is the length of the cuff (25, 26) or elastic laminate portion (10) when said cuff (25, 26) or portion (10) is stretched in y-direction to its maximum length, as set out herein.

"Absolute contracted length" is the length of the cuff (25, 26) or elastic laminate portion (10), when no stretching force is applied to it, e.g. when it is in relaxed state, flat on a surface.

The "z-direction" is perpendicular to the y-direction and substantially in the direction of the wrinkle height in the elastic laminate portion (10), and is herein also referred to as the height or thickness dimension.

The "x-direction" is perpendicular to both the x- and y-directions.

As used herein, "elastic" means, that the item is extendible or stretchable by application of a force in a certain direction and returns to at least 80% of its original length but to less than 150% of its original length in that direction, and typically to about its original size, after the stretching force is released.

As used herein, "along" means at least partially parallel and in close proximity or even in contact with.

As used herein "attached" includes "directly attached" and "indirectly attached", e.g. via attaching "a" to "b" by attaching "a" to "c" and "c" to "b".

Each embodiment defined by certain properties or dimension for which a value is defined herein is to be understood to include embodiments with functional equivalent properties or dimensions, e.g. a dimension of 0.5 cm has to be understood as meaning "about 0.5 cm".

The disposable absorbent article of the invention may be a sanitary napkin, panty-liner, or a diaper, i.e. an adult incontinence garment or infant diaper (as shown in the FIGS. 1 to 5) or training or pull-up pants. The article comprises the cuff (25, 26) with the supporting sheet (20) with an elastic laminate portion (10), that may be a leg cuff (25) and/or barrier cuff (26) and additional components, to have typically at least a backsheet (21), absorbent core (23) and a core cover sheet or topsheet.

The absorbent article of the invention comprises at least a (barrier or leg) cuff (25, 26) comprising at least one elastic laminate portion (10), formed from at least an elastic material (12) and a supporting sheet material (20) material, that itself is typically not elastically stretchable, said elastic laminate portion (10) having at least y-directional stretch (elongation), or only y-directional stretch, as shown in the Figures. Typically, the article comprises at least a pair of such, opposing cuffs 25, (26) that are each positioned along one longitudinal side, and spaced apart from the y-axis of the article The article may also comprise other components that comprise such an elastic laminate portion(s) (10) such as elastic waist band(s) (25) or side panels.

The longest dimension or length of the cuff (25, 26) and of the elastic laminate portion(s) (10) are typically parallel to the y-axis of the cuff (25, 26) and of the article and this is typically substantially parallel to the average direction of stretch of the elastic laminate portion (10) and cuff (25, 26). Said cuff (25, 26) may comprise more than one of such laminate portions (10), which each may or may not be identical.

The cuff (25, 26) may consist of a supporting sheet material (20) and the elastic material (s) (12) or it may comprise other components, such as for example attachment means, such as adhesive (14) attachment sheets etc, covering strips (13).

A preferred disposable absorbent articles of the invention is a diaper, including adult incontinent garments, pull-on or training diapers and baby or infant diapers with fasteners (as shown in the Figures) that may comprise an absorbent core (23); a liquid pervious core coversheet or topsheet, on the absorbent core (23); a liquid impervious backsheet (21); optionally (elastic) side panels (27), (elastic) leg cuffs (25), (elastic) waist feature (24), and a fastening system (28). The article as shown in FIG. 1 has a first waist region, a second waist region, opposed to the first waist region and a crotch region located between the first waist region and the second waist region, each being about ⅓ of the length of the article.

In preferred embodiments, the backsheet (21) is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the article while still preventing exudates from passing through the backsheet. Exemplary breathable materials may include materials such as woven webs, nonwoven webs, composite materials such as film-coated nonwoven webs, microporous films.

The core coversheet or topsheet is preferably compliant, soft-feeling, and non-irritating to the wearer's skin. Further, at least a portion of the core cover sheet is liquid pervious, permitting liquids to be absorbed by the absorbent core (23) underneath. A suitable core cover sheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the core cover sheet includes fibers, the fibers may be spunbond, carded, wet-laid, meltblown, hydroentangled, or otherwise processed as is known in the art.

Any portion of the core coversheet or the topsheet described herein may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" issued to Roe on Mar. 4, 1997. The lotion may function alone or in combination with another agent as the hydrophobizing treatment described above. The core coversheet and/topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson.

The absorbent core (23) may comprise any absorbent material which is generally compressible, conformable, non-irritating to the wearer's skin, and capable of absorbing and retaining liquids such as urine and other certain body exudates. The absorbent core may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt, and preferably at least superabsorbent polymers or absorbent gelling materials; or any other known absorbent material or combinations of materials. Preferred may be that the absorbent core comprises at least 80% by weight (based on the total content of material in the core, excluding the core wrap or cover sheet) of superabsorbent polymer or so-called absorbent gelling material.

The article may also include a fastening system (28) that maintains the first waist region and the second waist region in a configuration so as to provide lateral tensions about the circumference of the article to hold it on the wearer. The fastening system (28) preferably comprises a surface fastener such as tape tabs, hook and loop fastening components and/or hermaphroditic fastening components; although any other known fastening means are generally acceptable. In alternative embodiments, opposing sides of the article may be seamed or welded to form a pant. This allows the diaper to be used as a pull-on type diaper or training pant. Training pants are placed in position on the wearer by inserting the wearer's legs into the leg openings and sliding the training pant into position about the wearer's lower torso.

The article may also comprise side panels (27) that are preferably elastic extensible, and may be or comprise the elastic laminate portion (10) as described herein, to provide a more comfortable and contouring fit by initially conformably fitting the article to the wearer and sustaining this fit throughout the time of wear well past when it has been loaded with exudates since the elasticized or extensible side panels allow the sides of the article to expand and contract.

Cuffs (25 26) with the Elastic Laminate Portion(s) (10)

The cuff (25, 26) herein comprises at least one elastic laminate portion (10), as described herein. Preferred is that the article comprises at least two such cuffs (25 and/or 26) as also shown in the FIGS. 1 and 2.

Each laminate portion (10) has in relaxed/contracted state and in partially stretched state, including at an elongation $\epsilon$ of 0.5 as described herein below, at least one surface with wrinkles that face the user's body and may be in contact with the skin in use. The elastic laminate portion (10) may comprise two or more (preferably non-elastic) sheets of material that are attached to either surface of an elastic material, and the laminate portion than typically contains wrinkles on either surface of the elastic laminate portion.

The properties of said wrinkles described herein applies at least to the wrinkles of the body-facing surface of the elastic laminate portion (10), but may apply to both surfaces of said laminate (10).

Figure 4:
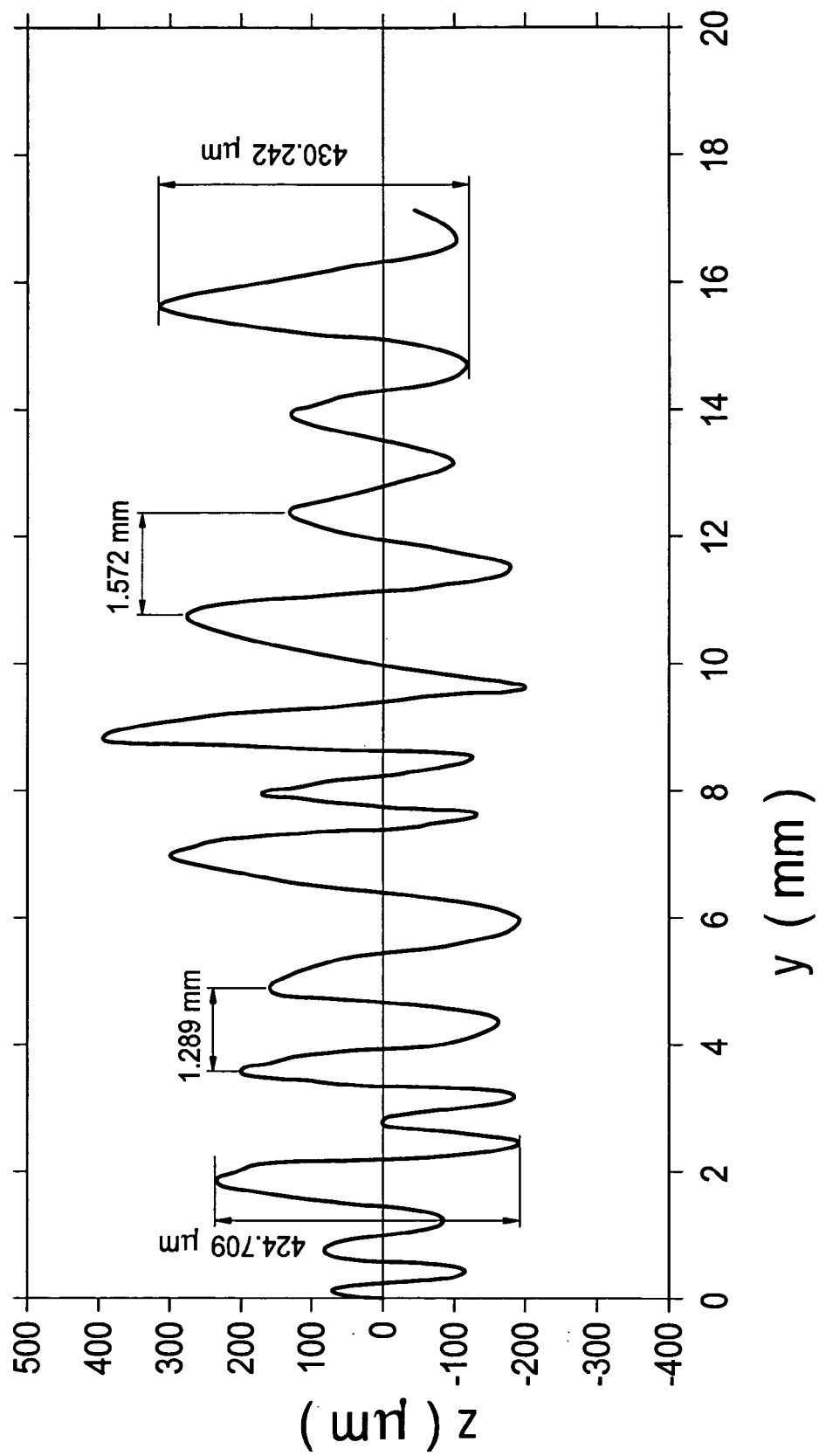
FIG. 4 shows the measurement results, obtained with the Primos method, using the Primos equipment and software, of a section of the elastic laminate portion (10), showing the wrinkle height and wrinkle width (and the there from derived density).

At an elongation $\epsilon$ of 0.5, whereby $\epsilon=(L_x-L_c)/L_c$, said wrinkles are of an average wrinkle height (as measured by the "Primos" method set below, using PRIMOS equipment) of less than 600 microns, and typically less than 600 but more than 200 microns, or between 550 microns and 300 microns, or up to 530, or even up to 500 microns. An exemplary Primos measurement graph of a section of an elastic laminate portion (10) as submitted by the test method herein is shown in FIG. 4.

At an elongation $\epsilon$ of 0.5, the elastic laminate portions (10) herein may have an average wrinkle density (wrinkles per cm) of from 5 to 10 wrinkles per cm or even from 6 to 10, or even 7 to 10, or possibly only up to 9 wrinkles per cm, as measured with the Primos method set out below.

The elastic laminate portions (10) of the invention have an average maximum elongation $\epsilon_{max}$, (being $(L_s-L_c)/L_c$ whereby $L_s$ is the fully stretched length of the elastic laminate portion), of at least 0.8 or even more preferably at least 1.0 or even more preferably at least 1.2, or it may be at least 1.4. These values can be obtained by the method set out in the method section below. It should be understood that the cuff (25, 26) may comprise areas (typically of between 0.5 and 2 cm, or 0.8 and 1.5 cm) where an elastic material is attached to the supporting sheet material without providing in that area any elongation of at least 0.5, and there are then possibly not even any wrinkles present. It should be understood for the purpose of the invention that such areas where elastic material is present but that have an elongation of less than 0.5 are not considered part of the elastic laminate portion (10) herein. Such areas may herein be referred to as "attachment portions".

In order to determine and obtain the elongation $\epsilon=0.5$ of the elastic laminate portion (10), the elastic laminate portion's (10) absolute contracted length $L_c$, is first determined as follows.

The cuff (25, 26) with the elastic laminate portion (10) is removed from the absorbent article, or if possible the elastic laminate portion (10) is removed from the article, either way such that the wrinkle profile and elastic profile (i.e. of the upward facing surface that in use is facing the body of the user) is not changed.

The cuff (25, 26) or elastic laminate portion (10) is placed as flat as possible on a surface, without applying any elongating or stretching force to it. Then, the absolute contracted length of the elastic laminate portion (10) of the cuff (25, 26) is measured. This is herein referred to as the absolute contracted length of the laminate $L_c$.

Then, the length of the laminate portion (10) at $\epsilon=0.5$ can be calculated, this being $1.5 L_c$
(based on: $\epsilon=(L_x-L_c)/L_c$).

Subsequently, the laminate portion (10) can be stretched by the method described herein below to obtain this elongation of 0.5 at $1.5 L_c$. Then, the wrinkle heights, average wrinkle height and deviations, wrinkle width, distance between wrinkles, average wrinkle density and deviation thereof can be calculated by use of the Primos method, using PRIMOS equipment, as described below.

Typically, the elastic laminate portion (10) has wrinkles of a relatively or substantially uniform wrinkle height (distribution), at least on the body-facing surface of the elastic laminate portion (10). For example, less than 10% or preferably less than 5% of the wrinkles are 800 microns or more, preferably less than 10% or even less than 5% of the wrinkles are 700 or more, or even 650 microns or more; and it may even be possible that 95% or more, or even all wrinkles (about 100%) have a height of less than 600 microns.

Furthermore, it may be preferred that the wrinkle density is substantially uniform throughout an elastic laminate portion e.g. that in no section of 2 cm (in length direction, along the laminate portion) the wrinkle density is more than 12 and that in no section of 2 cm (in length direction, along the laminate portion) the wrinkle density is less than 3, or less than 4. (Preferred may be that in each 2 cm section of a laminate portion (10) the wrinkle density is between 5 and 10, or any of the preferred values described above.

The width of the elastic laminate portions (10) will vary, typically depending on the exact dimensions of the cuff (25, 26) and/or of the article.

For example, for size 4 diapers the elastic laminate portion (10) in a cuff (25, 26) herein may, in fully stretched state, have an average width of about 1 to 3 mm.

The elastic materials (12) used herein are typically very thin, typically having a thickness or caliper (e.g. gauge) of typically up to about 200 microns, or even up to 150 microns or even up to 110 microns, or up to 100 microns and they may need to be at least 20 microns, more preferably at least 40 microns, or even at least 60 microns, as defined herein. Highly preferred materials have a thickness of about 70 to 100 microns.

A suitable elastic material is for example 2L-89, available from Fulflex, (Limerick, Ireland).

Figure 2:
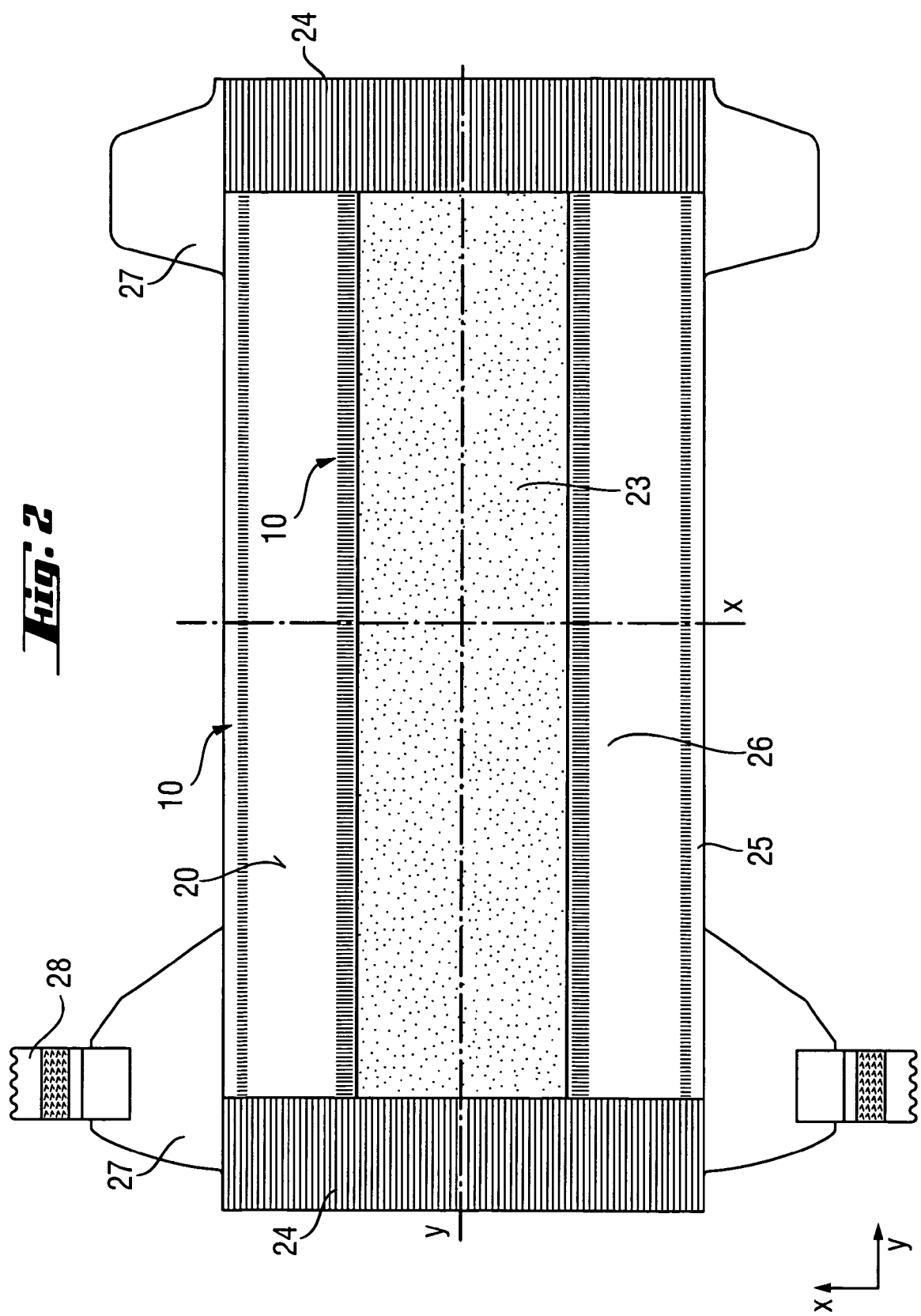
FIG. 2 shows a top view of an exemplary diaper of the invention

The article herein typically has a pair of barrier cuffs (25, 26) with the elastic laminate portions as described herein that are typically mirror images of one another mirrored in the y-axis, as shown in FIGS. 1 and 2. The barrier cuffs (26) may be attached to the leg cuffs (25), backsheet or topsheet in conventional manners, know in the art. It may be preferred that the barrier cuffs (26) comprise each two elastic laminate portions that are transversely spaced apart, both extending typically parallel in the direction of stretch. The may or may not be both elastic laminate portions (10) as described herein, however, typically at least the transverse outer elastic laminate portion (10) is as described herein. The article may alternatively or in addition comprise a pair of leg cuffs (25) with the elastic laminate portion described herein, that are also typically mirror images of one another mirrored in the y-axis.

The free (outer) longitudinal edge of the elastic laminate portion (10) or even the laminate portion (10) or cuff (25, 26) as a whole may have an average caliper (at a pressure of 0.33 psi and an elongation of 0.5) of 1.1 mm or less, or 1.0 mm or less, or 1.0 mm or less, or 0.95 mm (950 microns) or less, and it may be more than 0.4 mm (400 microns) or even for example more than 0.6 mm (600 microns), as measured with the method set out herein below.

Hereto, the elastic laminate portion (10) may comprise one or two (laminated) layers that each have a basis weight of 20 g/m$^2$ or less, preferably one or two (laminated) layers of a basis weight of 17 g/m$^2$ or less; provided that if two (laminated) layers are present, their combined basis weight may preferably be 34 g/m$^2$ or less.

Figure 3:
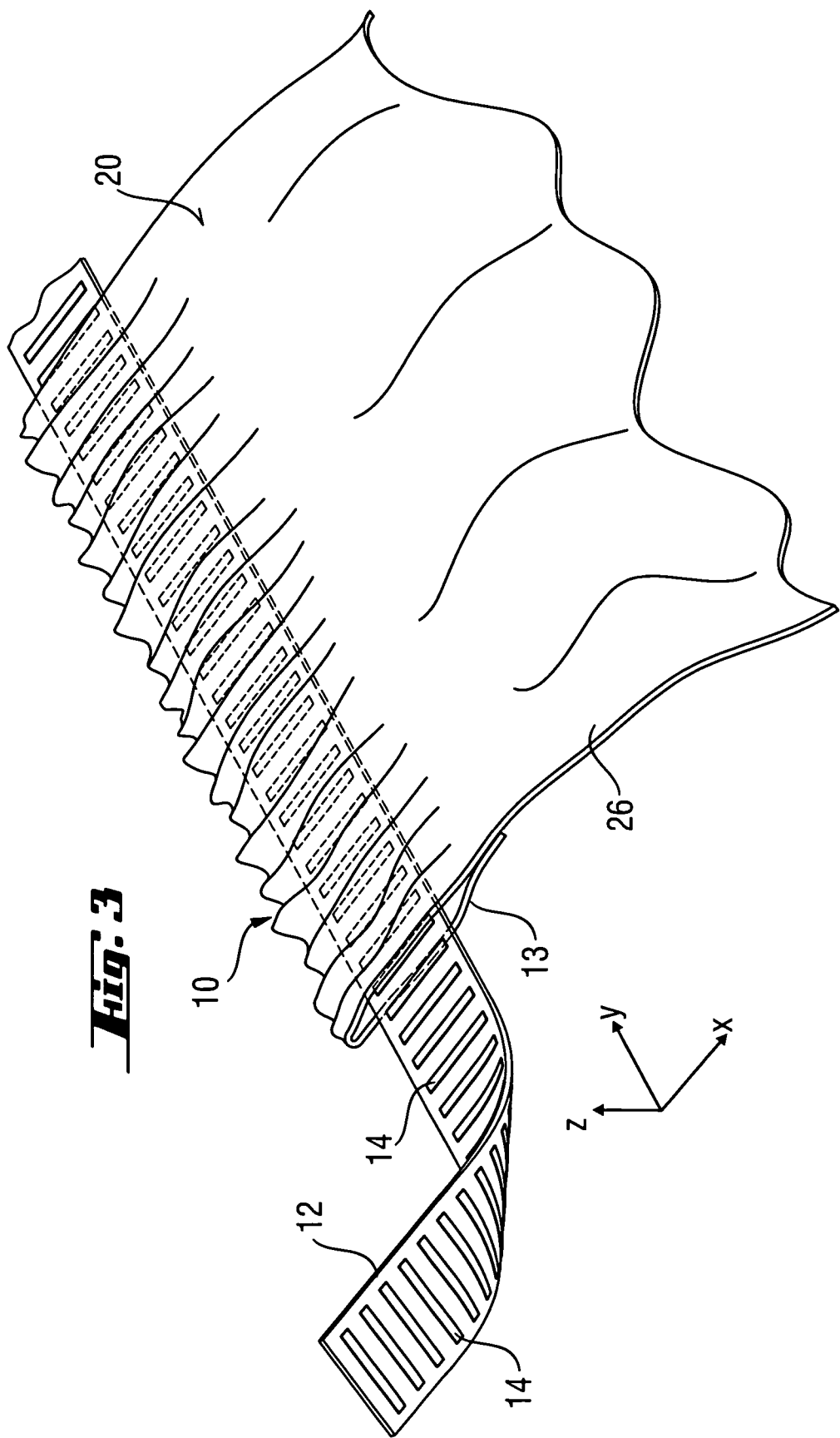
FIG. 3 shows a perspective view of section of a supporting sheet (20), for example the barrier cuff sheet (26) as shown in FIGS. 1 and 2, with an elastic laminate portion (10).

The cuff (25, 26) may also be made of two (laminated) layers, with therein between, in certain area(s), the elastic material (e.g. a so-called sandwich structure), as for example shown in FIG. 3. Then, for example, the cuff (25, 26) may be made of a single (laminated) layer of for example a basis weight of 20 g/m$^2$ or less, or one or two (laminated) layers of a basis weight of 17 g/m$^2$ or less.

The cuff (25, 26) as a whole may typically have an average caliper that is the same or less than the caliper of the laminate portion (10). The cuff (25, 26) and the elastic laminate portion (10) herein may comprise any sheet material suitable to be laminated to an elastic material (12). Preferably, the sheet material of the cuff (25, 26) and laminate portion(s) (10) is not itself elastically stretchable in y-direction.

The cuff (25, 26) is preferably air permeable. In certain executions herein, it may be preferably that it has high barrier properties. The cuff (25, 26) and the elastic laminate portion (10) is preferably hydrophobic and/or urine-impermeable.

Preferred supporting sheets (20), cuffs (25, 26) and elastic laminated portion(s) (10) thereof comprise woven and non-woven materials of natural fibers (e.g., wood or cotton fibers) and/or synthetic fibers. They comprise preferably thermoplastic polymer fibers, preferably selected from the group comprising: polyolefins, polyesters, polyurethanes, and polyamides, most preferably the thermoplastic polymer being a polyolefin, most preferably being polypropylene or polyethylene. The fibers may be spun bond, carded, wet-laid, melt blown, and/or hydro entangled, and/or otherwise processed as is known in the art. Preferred is that the cuff (25, 26) and laminate portion (10) thereof comprises one or more nonwoven material sheets that is itself a laminate of layers of meltbown and carded or spunbond material. For example, a sheet or layer of the cuff (25, 26) may be a laminate of at least two layers, one of which at least is a meltblown (M) layer and one of which is at least a spunbond(s) or a carded (C) layer.

Preferred executions are SM SMS, SMMS, SSMS, SSMSS, SSMMS, CM or CMC non-wovens laminates.

Most preferably, said non-woven webs are formed from polyethylene, polypropylene and/or polybutylene polymer fibers, or (a mixture of) fibers of a copolymers of polyethylene, polypropylene and/or polybutylene; most preferred are polypropylene polymer fibers.

It may also be preferred that the cuff (25, 26) comprises ingredients, which reduce friction between the wearer's skin and the cuff (25, 26), or in particular between the skin and the elastic laminate portion (10). Hereto, the laminate portion (10) or cuff (25, 26) may for example comprise a lotion, a fine powder, such as talcum powder, or wax.

The cuff (25, 26) or laminate portion (10) may be treated with an agent to reduce its surface energy. For example useful agent include fluorocarbons as described in U.S. Pat. No. 5,876,753, issued to Timmons et al. on Mar. 2, 1999; U.S. Pat. No. 5,888,591 issued to Gleason et al. on Mar. 30, 1999; U.S. Pat. No. 6,045,877 issued to Gleason et al. on Apr. 4, 2000. Other agents include silicone. Useful methods for applying the agent to the material, without reducing the air permeability, can be found in U.S. Pat. No. 5,322,729 and PCT Publication WO 96/03501. Preferred agents may be selected from the group comprising fluorocarbons, siloxanes, polysiloxanes, preferably including fluorinated monomers and fluorinated polymers, including hexafluoroethylene, hexafluoropropylene and vinyl fluoride and vinylidene fluoride, fluoroacrylate and fluoromethacrylate. Highly preferred is that the cuff (25, 26) is provided with poly(tetra)fluoroethylene, fluorinated ethylene-propylene copolymers and/or fluorinated ethylene-tetrafluoroethylene copolymers.

The cuff (25, 26) with the elastic laminate portion (10) and/or the laminate portion(s) (10) herein are such they typically have one of the following elastic profiles:

a) 1.5Lt by a first load force of less than 1.1N or even less than 0.6N, 3.0Lt by a first load force of less than 2.1N or even 1.1N and 4.5Lt by a first load force of less than 3.0N or even less than 1.5N and a second unload force at 4.5Lt of more than 0.9N, a second unload force at 3.0Lt of more than 0.5N and a second unload force at 1.5Lt of more than 0.1N. (Said elastic profile obtainable by the method set out in co-pending application EP1201212-A, whereby Lt is the contracted length of the cuff (25, 26) or elastic laminate portion (10), which ever applicable, herein referred to as $L_c$). or:

b) $0.25L_s$ by a first load force of less than 0.6 N, $0.55L_s$ by a first load force of less than 5N or even less than 3.5 N and $0.8L_s$ by a first load force of less than 10.0N or even less than 7.0N and a second unload force at $0.55L_s$ of more than 0.4N, and a second unload force at $0.80L_s$ of more than 1.4N, or even more than 2.0N.

(Said elastic profile obtainable by the method set out in co-pending application EP1201212-A, whereby $L_s$ is as specified herein, being the fully stretched length of the elastic laminate portion (10) or cuff (25, 26), which ever is applicable.)

Preferably, the cuff (25, 26) and/or elastic laminate portion (10) has a force profile such that it has a first load force at 200% elongation of 1.6 N or less, and a second unload force at 200% elongation of 0.5 N or more.

The elastic material (12) may be attached to one or more of the supporting sheet(s) or layers or nonwoven(s) that form the elastic laminate portion (10) or typically the cuff (25, 26), by any method, including adhesive bonding and ultrasonic bonding, but preferred may be the use of adhesive. The adhesive may be applied such that the required wrinkle density and wrinkle heights are achieved, as also claimed herein.

Preferred is that the elastic material (12) is attached to the supporting sheet material (20) comprised in the elastic laminate portion by use of a specific pattern that is suitable to obtain the wrinkle heights and densities referred to herein, said pattern having providing attachment areas (14) and non attachment areas therein between, as for example shown in FIGS. 5 and 6.

Preferred may be that the elastic laminate portion (10) has, at fully stretched absolute state with length $L_s$, substantially transverse attachment areas (14) such that the average distance between neighboring transverse parts of the attachment area(s) (14) is from 0.3 mm to 2.5 or to 2.0 mm, or preferably from 0.6 to 1.2 mm. Preferred may be that the average width (substantially in the direction of stretch), of the transverse parts (in the elastic laminate portion (10) at said fully stretched state), is from 0.2 mm to 1.2 mm, or preferably from 0.3 mm to 0.8 mm. or even 0.5 or less. Preferred may be that the ratio of the average width of the transverse attachment parts to the average distance between said attachment parts (ratio $R_{adhesive}$) is from about 4:10 to 8:10 or 6:10, or for example about 1:2

For example, the attachment means may include a uniform continuous layer of adhesive, a patterned layer of adhesive, or an array of separate lines, spirals, "omega" shaped line(s),or spots of adhesive. The adhesive may for example be applied in an intermittent stripe pattern, preferably straight stripes that are positioned in (substantially) transverse direction along the elastic laminate portion, e.g. substantially perpendicular to the longitudinal direction of the elastic laminate portion (10), as shown in FIG. 5. Preferred may be that the average distance between neighboring adhesive stripes (as shown attachment area (14), as also shown in FIG. 5) is from 0.3 mm to 2.5 or even to 2.0 mm, or preferably to 1.5 mm, or even from 0.6 to 1.2 mm. Preferred may be that the stripes are have on average a width (in y-direction of stretch) of less than 1.2 mm, preferably 0.3 to 0.8 mm, or even 0.5 mm or less.

Preferred may be that the ratio of the average width of the stripes to the average distance between neighboring stripes (ratio $R_{adhesive}$) is from about 4:10 to 8:10 or 6:10, or for example about 1:2

The adhesive may also be applied in a so-called omega pattern, as shown in FIG. 6, whereby each omega shaped part has a "loop", with a upwards "leg" and a downside "leg", departing from and arriving to an average "base-line". Hereby, the omega line itself may have an average width as described above for the width of the attachment areas (14) and the distance between the neighboring "legs of a loop or neighboring loops" may be as described above for the distance between the attachment areas (14) (and then each "leg" is considered an attachment area (14); or the distance between neighboring "loops" may be as described herein above for the distance between neighboring attachment areas (14) and the average width of a loop may be as described above for the average width of an attachment area (14) (and then the loop as a whole is an attachment area (14)). In either case, the $R_{adhaive}$ may also be as above.

The article may also comprise a waist band or feature (24) and/or side panels (27) that comprise one or more of the elastic laminate portions (10) as described herein. Then, the direction of stretch (herein referred to as y-direction) is perpendicular to the y-direction of the article. The side panels (27) may be comprised between and attached to the waistband (24) and the fasteners, or it may be comprised between and attached to two waistband portions (24). The side panels and/or waist band then are then also extendable with an extension of at least 0.8, as described above.

Test Methods:
Method to Stretch the Elastic Laminate Portion (10) to an Elongation of $\epsilon=0.5$;
Method to Determine Its Fully Stretched Length $L_s$ and $\epsilon_{max}$ The elastic laminate portion (10) may be straight, curved, or it may comprise several straight parts that are joined under one or more angles with one another, as can been seen in FIGS. 1 and 2, or it may have a combination of such configurations. This is herein referred to, respectively, as "straight", "curved" or "angled" elastic laminate portion (10), respectively, or for example, "curved and angled" elastic laminate portion (10) etc.

In each case below, a sample (e.g. cuff (26) or preferably an elastic laminate portion thereof, if this can be isolated as such) is obtained from an absorbent article that has been conditioned for 24 hours at 50% humidity and 23° C.

1) When the Elastic Laminate Portion (10) is Straight:
The elastic laminate portion (10) or cuff (25, 26) as a whole is obtained and put on a flat surface as described above to measure the contracted length of the elastic laminate portion (10) $L_c$.

The elastic laminate portion is subsequently elongated to 1.5 $L_c$ (equals $\epsilon=0.5$) or to its fully stretched length $L_s$, to determine $\epsilon_{max}$ as follows.

The sample (the cuff with the elastic laminate portion or the elastic laminate portion thereof) is left for 24 hours at 25° C. and 50% humidity, prior to the elongation/stretching step below, which is subsequently performed under the same conditions.

Measurement of lengths of the samples can be done with a micrometer screw.

The sample to be tested is placed length-wise (in the direction of stretch) between two tweezers or, if the width of the sample is more than 1 cm, between two clamps of a width of 1 cm, one on each end, such that contact area of the tweezers/clamp and the sample is at the most 1 mm for clamps and 0.5 mm for tweezers in the direction of stretch (length). The exact distance between the start of one clamp or tweezers to the beginning of the other clamp or tweezers is measured. This is the contracted length of the sample, e.g. of the laminate portion.

For straight samples, the clamps or tweezers are moved in the y-direction of the length of the straight samples, such that the length direction is the direction of the elongation force.

The sample may thus be stretched to its maximum elongation (e.g. when the cuff (25, 26) reaches its maximum length) and the length of the sample and the distance between the clamps is measured, and the elongation $\epsilon_{max}$ is calculated.

Alternatively, the sample is stretched to $\epsilon=0.5$, in order to submit the thus stretched sample to the Primos method set out below.

2) When the Elastic Laminate Portion (10) is "Angled":
The elastic laminate portion (10) is divided by marking with a fine marker pen into straight parts (i.e. between the angles), for example in 3 straight parts. The sample is prepared and conditioned as described above.

Subsequently, each straight part is elongated separately by the method set out above for straight elastic laminate portions (10) to either $\epsilon=0.5$ or $\epsilon_{max}$, e.g. when the sample comprises two angles and 3 straight parts, 3 force lines are determined and the sample is stretched 3 steps.

3) When the Elastic Laminate Portion (10) is Curved:
The curved elastic laminate portion (10) is divided with a fine marker pen into sections of 2 cm absolute length and possibly one remaining section of a smaller length. The sample is prepared and conditioned as described above.

Prior to elongation, the force line of each section of 2 cm (or one section of less than 2 cm) is determined as follows. Each section has two transverse edge lines that are 2 cm apart, and each transverse edge line has a center point. A line can be drawn through said two points of said two transverse edge lines. This will be the "y-direction line" or force line along which the force will be applied to elongate said section. This will be done for each section.

Subsequently, each section is elongated separately by the manner set out above for straight elastic laminate portions (10), but by separately elongating each section along its own force line, to either $\epsilon=0.5$ or its maximum elongation $\epsilon_{max}$.

After stretching all sections, a fully stretched absolute length can be measured for each section and for the elastic laminate portion (10), $L_s$ and $\epsilon_{max}$ can be calculated.

4) Mixed Elastic Laminate Portion (10)

If the elastic laminate portion (10) comprises a combination of curved, angled and/or straight parts, then a combination of the above methods is applied accordingly.

Primos Method:
Determination of the Wrinkle Heights and Density Averages and Deviations thereof The following described the method to determine the wrinkle height and winkle density of the laminate portion (10) of the cuff (25, 26).

Each sample with the elongation of 0.5 as defined and obtained by the method described herein, is examined by use of PRIMOS equipment and its data acquisition software, following the manufacture's instructions manual, using a 13×18 mm lens.

If the elastic laminate portion (10) has an average width of more than 3 mm, then the measurement above is only done on the inner 70% of the width of the laminate portion, along its length.

The PRIMOS equipment will provide graphs per measured section of the sample, as shown in FIG. 4, and it provides exact values per wrinkle, e.g. height, width, and it allows to calculate the average of wrinkles per cm, wrinkle height, deviations etc.

Caliper Measurement

The caliper and average caliper of an elastic laminate portion (10) that has an elongation of $\epsilon=0.5$, as described herein, can be obtained by use of a micrometer, such as the Frank 16303, obtainable from Twing Albert-Frank GmbH. The test is done at 23° C., 50% humidity. The sample should be already conditioned to this humidity and temperature as set out above, since it has been conditioned for 24 hours under these conditioned, prior to stretching it to the required elongation of 0.5, needed to do this caliper test. The equipment is calibrated prior to testing. The lowering speed of the pressure foot is set to be 3 mm/sec and the dwelling time 2-5 sec.

The size (surface area) of the anvil is chosen depending on the size of the elastic laminate potion (10), and subsequently the weight on the pressure foot is chosen such that the required pressure of 0.33 psi is obtained.

For example, an anvil with a 40 mm diameter is used and a total weight of 295 grams (80 grams of the pressure foot plus an additional 115 grams) is applied to measure preferred elastic laminate portion(s) (10) herein.

To obtain the average caliper of the elastic laminate portion, the test is repeated on several portions of the elastic laminate portion, such that the areas pressed by the anvil per measurement do not overlap. Subsequently, an average can be calculated. Also the deviation in the caliper can be calculated.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising a backsheet and an absorbent core and a topsheet, that in use faces the wearer, a crotch region between first and second waist regions, elastic side panels joined to one of said first and second waist regions, a pair of leg cuffs, and a pair of barrier cuffs situated laterally inwardly of the leg cuffs, each of said leg cuffs and said barrier cuffs comprising one or more longitudinally extending elastic laminate portion, formed by a flat strip of an elastic material attached to a supporting sheet of said cuff, said strip of elastic material having a thickness of at least about 20 microns and less than 100 microns, said laminate portion comprising in at least relaxed and partially contracted state a body-facing surface with a multitude of wrinkles, and wherein said elastic laminate portion has an absolute contracted length $L_c$, a fully stretched absolute length $L_s$, and an average caliper (at 0.33 psi and at an elongation $\epsilon=0.5$) from 0.4 mm to 1.1 mm,
whereby at a partial elongation of the elastic laminate potion of $\epsilon=0.5$:
a) said wrinkles have an average wrinkle height $H_w$ of more than 200 micrometers and less than 600 micrometers;
b) said elastic laminate portion has an average wrinkle density $D_w$ between 5 and 10 wrinkles per cm; and
c) 95% or more of said wrinkles have a height of less than 600 microns;
wherein said elastic laminate portion comprises one or more nonwoven material sheet, the nonwoven material sheet being a laminate of layers of meltblown material and carded or spunbound material.

2. A disposable absorbent article according to claim 1, wherein said nonwoven laminate sheet has a basis weight of 22 g/mm$^2$ or less.

3. A disposable article according to claim 1, wherein one such elastic laminate portion is positioned, and longitudinally extending, along the outer edge of each cuff.

4. A disposable absorbent article according to claim 1, wherein said elastic is attached to the cuff by use of an adhesive that is applied in the form of an omega pattern with transverse loop parts that provide transverse attachment areas wherein at fully stretched state Ls, the average distance between neighboring transverse attachment areas is between 0.3 to 2.2 mm.

5. A disposable absorbent article according to claim 4, wherein the average width (in y-direction; at fully stretched state) is between 0.3 mm and 0.8 mm.

6. A disposable absorbent article according to claim 1, Wherein at least one of said cuffs and said elastic laminate portion is hydrophobic.

7. A disposable absorbent article according to claim 1 whereby the cuff has a force profile such that it has a first load force at 200% elongation of 1.6 N or less, and a second unload force at 200% elongation of 0.5 N or more.

8. A disposable absorbent article according to claim 1 wherein said article is chosen from one of a diaper and a pant.

9. A disposable absorbent article according to claim 1 wherein said side panels comprise a fastening system that holds the article about the waist of a wearer during use of the article.

10. A disposable absorbent article comprising a backsheet and an absorbent core, a topsheet that in use faces the wearer, a pair of leg cuffs, and a pair of barrier cuffs situated laterally inwardly of the leg cuffs, a waist band and a side panel wherein at least one of said cuffs, waist band and side panel comprises an elastic laminate portion formed by a flat strip of an elastic material attached to a supporting sheet of said leg cuffs, waist band or side panel, said strip of elastic material having a thickness of at least about 20 microns and less than 100 microns, said elastic laminate portion having stretch in a direction perpendicular to the y-direction of the article, whereby said laminate portion comprises in at least relaxed and partially contracted state body-facing surface with a multitude of wrinkles, and Wherein said elastic laminate portion has an absolute contracted length $L_c$ (in the direction of stretch), a fully stretched absolute length $L_s$, and an average caliper (at 0.33 psi and at an elongation $\epsilon=0.5$) from 0.4 mm to 1.1 mm,
  wherein at a partial elongation of the elastic laminate portion of $\epsilon=0.5$:
  a) said wrinkles have an average wrinkle height $H_w$ of more than 200 micrometers and less than 600 micrometers;
  b) said laminate portion has an average wrinkle density $D_w$ between 5 and 10 wrinkles per cm; and
  c) 95% or more of said wrinkles have a height of less than 600 microns;
  wherein said elastic laminate portion comprises one or more nonwoven material sheet, the nonwoven material sheet being a laminate of layers of meltblown material and carded or spunbound material.

11. A disposable absorbent article according to claim 10 wherein said article is chosen from one of a diaper and a pant.

12. A disposable absorbent article according to claim 10 wherein said side panels comprise a fastening system that holds the article about the waist of a wearer during use of the article.

13. A disposable absorbent article adapted to be worn by a wearer comprising:
  a backsheet;
  an absorbent core;
  a topsheet that in use faces the wearer;
  a crotch region between first and second waist regions,
  elastic side panels joined to one of said first and second waist regions;
  a pair of leg cuffs; and
  a pair of barrier cuffs situated laterally inwardly of the leg cuffs;
  wherein each of said barrier cuffs comprises at least one longitudinally extending elastic laminate portion, formed by a flat strip of an elastic material attached to a supporting sheet, said strip of elastic material having a thickness of at least about 20 microns and less than 100 microns, said laminate portion comprising a plurality of wrinkles and having an average caliper (at 0.33 psi and at an elongation $\epsilon=0.5$) from 0.4 mm to 1.1 mm, wherein at a partial elongation of the elastic laminate potion of $\epsilon=0.5$:
  a) said wrinkles have an average wrinkle height $H_w$ of more than 200 micrometers and less than 600 micrometers;
  b) said laminate portion has an average wrinkle density $D_w$ between 5 and 10 wrinkles per cm; and
  c) 95% or more of said wrinkles have a height of less than 600 microns;
  wherein said elastic laminate portion comprises one or more nonwoven material sheet, the nonwoven material sheet being a laminate of layers of meltblown material and carded or spunbound material.

* * * * *